(12) United States Patent
Rajguru et al.

(10) Patent No.: US 12,178,642 B2
(45) Date of Patent: Dec. 31, 2024

(54) DISEASE SPECIFIC AND TREATMENT TYPE SPECIFIC CONTROL OF INTRALUMINAL ULTRASOUND IMAGING

(71) Applicant: VOLCANO CORPORATION, San Diego, CA (US)

(72) Inventors: Nikhil Sreedhar Rajguru, San Diego, CA (US); Pei-Yin Chao, Eindhoven (NL)

(73) Assignee: PHILIPS IMAGE GUIDED THERAPY CORPORATION, San Diego, CA (US)

( * ) Notice: Subject to any disclaimer, the term of this patent is extended or adjusted under 35 U.S.C. 154(b) by 137 days.

(21) Appl. No.: 16/663,541

(22) Filed: Oct. 25, 2019

(65) Prior Publication Data

US 2020/0129144 A1 Apr. 30, 2020

Related U.S. Application Data

(60) Provisional application No. 62/750,890, filed on Oct. 26, 2018.

(51) Int. Cl.
| | |
|---|---|
| *A61B 8/08* | (2006.01) |
| *A61B 8/00* | (2006.01) |
| *A61B 8/12* | (2006.01) |

(52) U.S. Cl.
CPC .......... *A61B 8/0891* (2013.01); *A61B 8/0841* (2013.01); *A61B 8/12* (2013.01);
(Continued)

(58) Field of Classification Search
CPC ....... A61B 8/0891; A61B 8/0841; A61B 8/12; A61B 8/463; A61B 8/469; A61B 8/5207; A61B 8/085; A61B 8/465; A61B 8/5215
See application file for complete search history.

(56) References Cited

U.S. PATENT DOCUMENTS

| | | |
|---|---|---|
| 6,200,268 B1 | 3/2001 | Vince |
| 6,381,350 B1 | 4/2002 | Klingensmith |

(Continued)

FOREIGN PATENT DOCUMENTS

WO 2019175004 A1 9/2019

OTHER PUBLICATIONS

Robert V. Kolecki, Determining the acuteness and stability of deep venous thrombosis by ultrasonic tissue characterization, Journal of Vascular Surgery, vol. 21, Issue 6, 1995, pp. 976-984 (Year: 1995).*

*Primary Examiner* — Joel Lamprecht
*Assistant Examiner* — Brooke Lyn Klein

(57) ABSTRACT

An intraluminal ultrasound imaging system includes a processor circuit configured for communication with an intraluminal ultrasound imaging catheter, and is configured to receive an intraluminal ultrasound image obtained by the imaging catheter while the intraluminal ultrasound imaging catheter is positioned within a body lumen of a patient. The processor circuit is further configured to output, to a display in communication with the processor circuit, at least two image type options, receive a user selection of an image type option, select a preset value for at least one image processing parameter based on the image type option, and display the intraluminal ultrasound image according to the image processing parameter.

21 Claims, 8 Drawing Sheets

(52) U.S. Cl.
CPC .............. *A61B 8/463* (2013.01); *A61B 8/469* (2013.01); *A61B 8/5207* (2013.01)

(56) References Cited

U.S. PATENT DOCUMENTS

| | | |
|---|---|---|
| 7,074,188 B2 | 7/2006 | Nair |
| 7,175,597 B2 | 2/2007 | Vince |
| 7,215,802 B2 | 5/2007 | Klingensmith |
| 7,359,554 B2 | 4/2008 | Klingensmith |
| 7,463,759 B2 | 12/2008 | Klingensmith |
| 7,846,101 B2 | 12/2010 | Eberle |
| 2005/0249391 A1* | 11/2005 | Kimmel .................... G06T 7/11 382/128 |
| 2008/0154131 A1* | 6/2008 | Lee ........................ A61B 34/20 600/439 |
| 2012/0108964 A1* | 5/2012 | Lee .................... G01S 7/52033 600/437 |
| 2013/0281832 A1* | 10/2013 | Baumgart ............ A61B 6/4417 600/424 |
| 2014/0177935 A1* | 6/2014 | Nair .................... A61B 8/0883 382/132 |
| 2014/0180032 A1* | 6/2014 | Millett ................. A61B 8/4416 600/301 |
| 2015/0133776 A1* | 5/2015 | Hoffman ................ A61B 5/743 600/425 |
| 2015/0196271 A1* | 7/2015 | Nair .................... A61B 8/0841 600/439 |
| 2016/0166232 A1 | 6/2016 | Merritt |
| 2017/0360397 A1 | 12/2017 | Rothberg |
| 2019/0282199 A1 | 9/2019 | Merritt |

* cited by examiner

DISEASE SPECIFIC AND TREATMENT TYPE SPECIFIC CONTROL OF INTRALUMINAL ULTRASOUND IMAGING

CROSS REFERENCE TO RELATED APPLICATION

This application claims priority to and the benefit of U.S. Provisional Patent Application No. 62/750,890, filed Oct. 26, 2018, which is incorporated by reference herein in its entirety.

TECHNICAL FIELD

The subject matter described herein relates to a system for medical imaging. In particular, the disclosed system permits the automatic pre-selection of intraluminal ultrasound imaging control parameters by permitting a user to specify a particular disease type or treatment type. This system has particular but not exclusive utility for diagnosis and treatment of vascular diseases.

BACKGROUND

Different diseases or medical procedures produce physical features with different size, structure, density, water content, and accessibility for imaging sensors. For example, a deep-vein thrombosis (DVT) produces a clot of blood cells, whereas post-thrombotic syndrome (PTS) produces webbing or other residual structural effects in a vessel that have similar composition to the vessel wall itself, and may thus be difficult to distinguish from the vessel wall. A stent is a dense (e.g., metallic) object placed in a vessel or lumen to hold the vessel or lumen open to a particular diameter. Imaging parameters appropriate to show placement of a stent in a vessel may not show features of DVT or PTS, whereas imaging parameters appropriate to show the size and placement of a DVT may be inappropriate for imaging either a stent or a PTS. For example, imaging a DVT with an ultrasound imaging sensor may require ringdown, high gain, and low contrast, whereas imaging a PTS may require moderate gain, low contrast, and optional ringdown, and imaging a stent may require ringdown subtraction, low gain, and high contrast. Often practitioners using intravascular ultrasound systems have to change settings such as gain (brightness), field of view (depth), labels, annotations, etc. based on the case in question. Current systems present users with many options to fine tune these settings, but often these take up additional time and also depend on the expertise of the user to adjust these settings for optimized use in particular cases.

Generally speaking, a medical practitioner must adjust these parameters in real time during a medical imaging procedure, and save the resulting images to a storage medium. Raw imaging data is extremely voluminous and is generally not saved, so many parameters cannot be altered during post-processing of images, and thus clinically significant image detail may be lost.

The information included in this Background section of the specification, including any references cited herein and any description or discussion thereof, is included for technical reference purposes only and is not to be regarded as subject matter by which the scope of the disclosure is to be bound.

SUMMARY

Disclosed is a system for pre-selecting intraluminal imaging system control parameters by specifying a particular disease type or treatment type—the system hereinafter referred to as a case-specific imaging presets system. For example, the present disclosure describes disease-type-specific settings for the acquisition and display of peripheral intravascular ultrasound (IVUS) images. According to at least one embodiment of the present disclosure, a system is provided for pre-selecting intraluminal ultrasound image control parameters by specifying a particular disease type or treatment.

The case-specific imaging presets system disclosed herein has particular, but not exclusive, utility for intraluminal ultrasound imaging procedures. One general aspect of the case-specific imaging presets system includes an intraluminal ultrasound imaging system, including: a processor circuit configured for communication with an intraluminal ultrasound imaging catheter, where the processor circuit is configured to: receive an intraluminal ultrasound image obtained by the intraluminal ultrasound imaging catheter while the intraluminal ultrasound imaging catheter is positioned within a body lumen of a patient; output, to a display in communication with the processor circuit, a user interface including at least two image type options; receive, via the user interface, a selection of an image type option; select a preset value for at least one image processing parameter based on the image type option, where the at least one image processing parameter determines a visual aspect of how the intraluminal ultrasound image is displayed on the display, where each image processing parameter determines a different visual aspect; and output, to the display, the intraluminal ultrasound image such that the intraluminal ultrasound image is displayed according to the visual aspect. Other embodiments of this aspect include corresponding computer systems, apparatus, and computer programs recorded on one or more computer storage devices, each configured to perform the actions of the methods.

Implementations may include one or more of the following features. The system where the processor circuit is configured to output the intraluminal ultrasound image such that a feature in the intraluminal ultrasound image is enhanced based on the selected image type option. The system where the feature includes a stent. The system may where the processor circuit is configured to output the intraluminal ultrasound image such that the stent in the intraluminal ultrasound image is enhanced based on the selected image type option. The system where the feature includes anatomy in the intraluminal ultrasound image. The system where the processor circuit is configured to output the intraluminal ultrasound image such that the anatomy in the intraluminal ultrasound image is enhanced based on the selected image type option. The system where the anatomy includes at least one of a plaque, lesion, sub-acute thrombus, acute thrombus, chronic thrombus, webbing, scarring, deep vein thrombosis, compression, non-thrombotic iliac vein lesion, post-thrombotic syndrome, or chronic total occlusion. The system where the processor circuit is configured to output the intraluminal ultrasound image such that at least one of the plaque, lesion, sub-acute thrombus, acute thrombus, chronic thrombus, webbing, scarring, deep vein thrombosis, compression, non-thrombotic iliac vein lesion, post-thrombotic syndrome, or chronic total occlusion in the intraluminal ultrasound image is enhanced based on the selected image type option. The system where the user interface further includes a detection option associated with the feature. The system where, in response to the processor circuit receiving a selection of the detection option, the processor circuit is configured to identify the feature in the intraluminal ultrasound image. The system where the processor circuit is configured to identify the feature based on an occlusion threshold. The system where at least one of the at least two image type options in the user interface corresponds to an anatomical system of the intraluminal ultrasound image. The system where the at least two image type options in the user interface include coronary vasculature, peripheral venous vasculature, or peripheral arterial vasculature. The system where the at least one image processing parameter includes at least one of ringdown, gain curve, contrast, saturation, hue, field of view, or chroma. The system where the processor circuit is configured to change the visual aspect of the intraluminal ultrasound image based on at least one of the ringdown, gain curve, brightness, contrast, saturation, hue, field of view, or chroma. The system further including the intraluminal ultrasound imaging catheter. Implementations of the described techniques may include hardware, a method or process, or computer software on a computer-accessible medium.

One general aspect includes an intraluminal ultrasound imaging method, the method including: receiving, at a processor circuit, an intraluminal ultrasound image obtained by an intraluminal ultrasound imaging catheter while the intraluminal ultrasound imaging catheter is positioned within a body lumen of a patient; outputting, to a display in communication with the processor circuit, a user interface including at least two image type options; receiving, via the user interface, a selection of an image type option; selecting a preset value for at least one image processing parameter based on the image type option, where the at least one image processing parameter determines a visual aspect of how the intraluminal ultrasound image is displayed on the display, where each image processing parameter determines a different visual aspect; and outputting, to the display, the intraluminal ultrasound image such that the intraluminal ultrasound image is displayed according to the visual aspect. Other embodiments of this aspect include corresponding computer systems, apparatus, and computer programs recorded on one or more computer storage devices, each configured to perform the actions of the methods.

Implementations may include one or more of the following features. The method where the image type option is selected to enhance a feature in the image, the feature including at least one of a stent, plaque, lesion, sub-acute thrombus, acute thrombus, chronic thrombus, webbing, scarring, deep-vein thrombosis, compression, non-thrombotic iliac vein lesion, post-thrombotic syndrome, or chronic total occlusion. The method where the user interface further includes a detection option associated with the feature, and where the method further includes: identifying, by the processor circuit, the feature in the intraluminal ultrasound image in response to receiving a selection of the detection option. The method where identifying the feature is based on an occlusion threshold. The method where outputting the user interface includes outputting the at least two image type options including two or more of: coronary vasculature, peripheral venous vasculature, or peripheral arterial vasculature. The method where the at least one the image processing parameter includes at least one of ringdown, gain curve, brightness, contrast, saturation, hue, field of view, or chroma. Implementations of the described techniques may include hardware, a method or process, or computer software on a computer-accessible medium.

One general aspect includes an intravascular ultrasound imaging system, including: an intravascular ultrasound imaging catheter configured to obtain an intravascular ultrasound image while the intravascular ultrasound imaging catheter is positioned within a blood vessel of a patient; a processor circuit configured for communication with the intravascular ultrasound imaging catheter, where the processor circuit is configured to: receive the intravascular ultrasound image obtained by the intravascular ultrasound imaging; output, to a display in communication with the processor circuit, a user interface including at least two image type options identifying the blood vessel as coronary vasculature, peripheral venous vasculature, or peripheral arterial vasculature; receive, via the user interface, a selection of an image type option; select preset values for a plurality of image processing parameters based on the image type option, where the plurality of image processing parameters determine visual aspects of how the intravascular ultrasound image is displayed on the display, where each image processing parameter determines a different visual aspect, where the plurality of image processing parameters include two or more of ringdown, gain curve, field of view, or chroma; and output, to the display, the intravascular ultrasound image such that the intravascular ultrasound image is displayed according to the visual aspect. Other embodiments of this aspect include corresponding computer systems, apparatus, and computer programs recorded on one or more computer storage devices, each configured to perform the actions of the methods.

This Summary is provided to introduce a selection of concepts in a simplified form that are further described below in the Detailed Description. This Summary is not intended to identify key features or essential features of the claimed subject matter, nor is it intended to limit the scope of the claimed subject matter. A more extensive presentation of features, details, utilities, and advantages of the case-specific imaging presets system, as defined in the claims, is provided in the following written description of various embodiments of the disclosure and illustrated in the accompanying drawings.

BRIEF DESCRIPTION OF THE DRAWINGS

Illustrative embodiments of the present disclosure will be described with reference to the accompanying drawings, of which.

DETAILED DESCRIPTION

Figure 1:
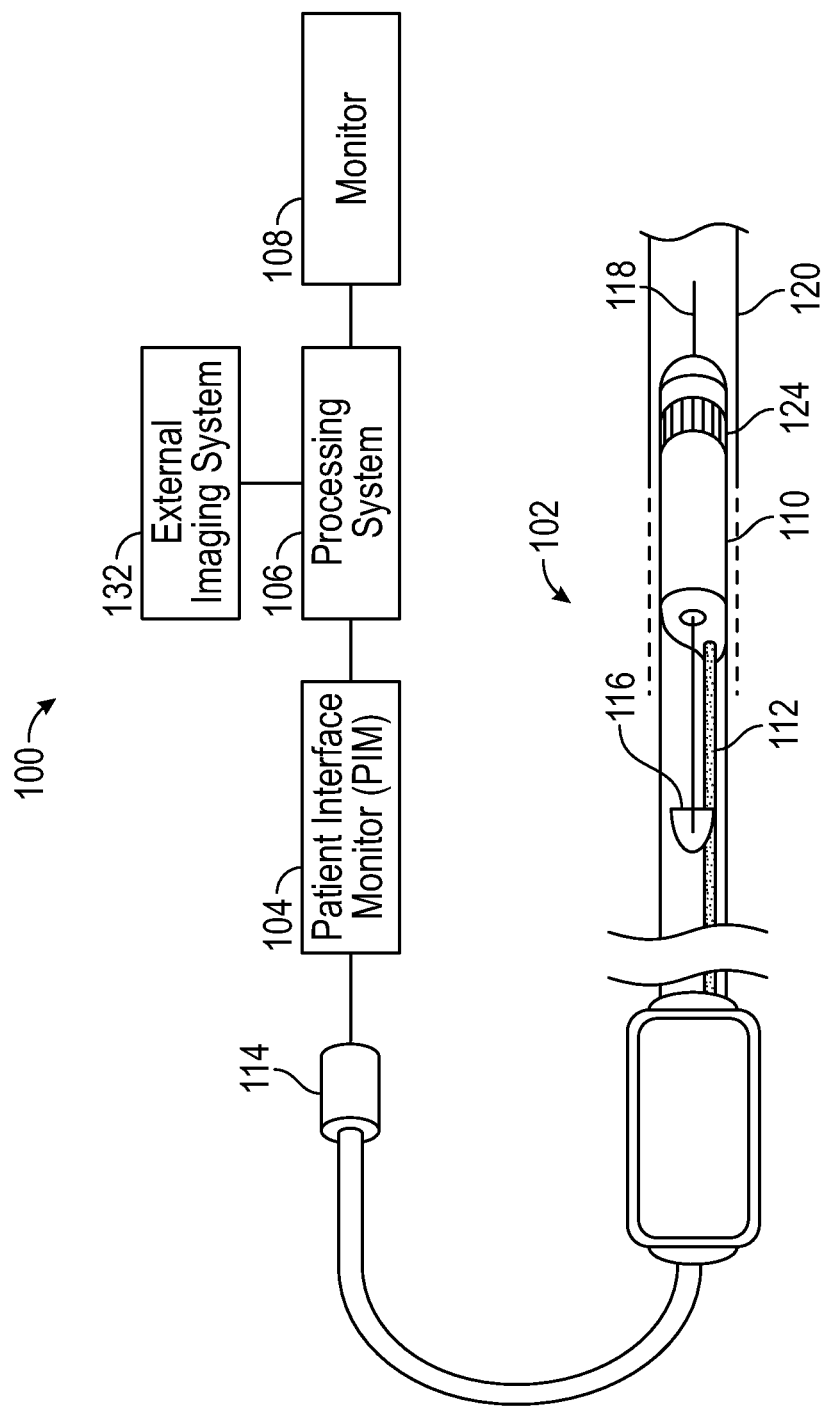
FIG. 1 is a diagrammatic schematic view of an intraluminal imaging system, according to aspects of the present disclosure.

The present disclosure relates generally to medical imaging, including imaging associated with a body lumen of a patient using an intraluminal imaging device. For example, the present disclosure describes disease type settings for acquisition and display of peripheral intravascular ultrasound or IVUS images. In accordance with at least one embodiment of the present disclosure, a system is provided for pre-selecting intraluminal ultrasound control parameters by specifying a particular disease type or treatment type— the system hereinafter referred to as a case-specific imaging presets system.

The devices, systems, and methods described herein can include one or more features described in U.S. Provisional App. No. 62/750,983, filed 26 Oct. 2018, U.S. Provisional App. No. 62/751,268, filed 26 Oct. 2018, U.S. Provisional App. No. 62/751,289, filed 26 Oct. 2018, U.S. Provisional App. No. 62/750,996, filed 26 Oct. 2018, U.S. Provisional App. No. 62/751,167, filed 26 Oct. 2018, and U.S. Provisional App. No. 62/751,185, filed 26 Oct. 2018, each of which is hereby incorporated by reference in its entirety as though fully set forth herein.

The devices, systems, and methods described herein can also include one or more features described in U.S. Provisional App. No. 62/642,847, filed Mar. 14, 2018 (and a Non-Provisional application filed therefrom on Mar. 12, 2019 as U.S. Ser. No. 16/351,175), U.S. Provisional App. No. 62/712,009, filed Jul. 30, 2018, U.S. Provisional App. No. 62/711,927, filed Jul. 30, 2018, and U.S. Provisional App. No. 62/643,366, filed Mar. 15, 2018 (and a Non-Provisional application filed therefrom on Mar. 15, 2019 as U.S. Ser. No. 16/354,970), each of which is hereby incorporated by reference in its entirety as though fully set forth herein.

The present disclosure aids substantially in capturing, recording, and annotating medical images (particularly though not exclusively intraluminal ultrasound images), by auto-selecting parameters such as scanning, imaging, and image processing parameters, as well as improving workflow by auto-selecting menu options and annotation parameters. Implemented on a medical imaging console (e.g., an intraluminal imaging console) in communication with medical imaging sensor (e.g., an intraluminal ultrasound sensor), the case-specific imaging presets system disclosed herein provides both time savings and an improvement in the quality of captured images. This improved imaging transforms raw imaging data into disease-specific and/or treatment-specific processed images that suppress unwanted or clinically insignificant image features, or that enhance or highlight important diagnostic image features, either in real time during the imaging procedure or during playback or review. This occurs without the normally routine need to fiddle manually with image settings, and greatly reduces problems associated with discarding raw image data and storing only processed images. This unconventional approach improves the functioning of the medical imaging console and sensor, by permitting disease-specific and treatment-specific optimization of images and workflow, without the system operator having to take any specific action other than identifying a disease or treatment type.

The case-specific imaging presets system may be implemented as a set of logical branches and mathematical operations, whose outputs are viewable on a display, and operated by a control process executing on a processor that accepts user inputs from a keyboard, mouse, or touchscreen interface, and that is in communication with one or more medical imaging sensors (e.g., intraluminal ultrasound sensors). In that regard, the control process performs certain specific operations in response to different inputs or selections made by a user at the start of an imaging procedure, and may also respond to inputs made by the user during the procedure. Certain structures, functions, and operations of the processor, display, sensors, and user input systems are known in the art, while others are recited herein to enable novel features or aspects of the present disclosure with particularity.

The present disclosure helps overcome the barriers of expertise in system handling, image interpretation and extended workflows by providing ways to better the image interpretation and the ease of use of the intravascular ultrasound systems by providing presets that are specific to common types or categories of clinical cases. In some embodiments, the disclosed system also allows the user to also change and save favorite settings based on personal/hospital preference.

Various types of intraluminal imaging systems are used in diagnosing and treating diseases. For example, intravascular ultrasound (IVUS) imaging is used as a diagnostic tool for visualizing vessels within a body of a patient. This may aid in assessing diseased or compressed vessels, such as arteries or veins, within the human body to determine the need for treatment, to optimize treatment, and/or to assess a treatment's effectiveness (e.g., through imaging of the vessel before and after treatment). Image processing of intraluminal medical images may occur while the images or being captured, or later during a review or playback mode. Different image processing parameters control different visual aspects of the processed medical image, including but not limited to brightness, contrast, saturation, gain, hue, ringdown, field of view, magnification, and enhancement of particular features, and can include changing the behavior of the transducer array, signal processing on the signal from the transducer array, and/or image processing on the image data generated from the signal. Selecting an image preset may for example permit simultaneous selection of values or parameters related to ringdown, gain curve (e.g., the relationship between input intensity values and output intensity values), field of view, and selecting multiple values for chroma (e.g., value for range, and value for depth).

In some cases, intraluminal imaging is carried out with an IVUS device including one or more ultrasound transducers. The IVUS device may be passed into the vessel and guided to the area to be imaged. The transducers emit ultrasonic energy and receive ultrasound echoes reflected from the vessel. The ultrasound echoes are processed to create an image of the vessel of interest. The image of the vessel of interest may include one or more lesions or blockages in the vessel. A stent may be placed within the vessel to treat these blockages and intraluminal imaging may be carried out to view the placement of the stent within the vessel. Other types of treatment include thrombectomy, ablation, angioplasty, pharmaceuticals, etc.

These descriptions are provided for exemplary purposes only, and should not be considered to limit the scope of the case-specific imaging presets system. Certain features may be added, removed, or modified without departing from the spirit of the claimed subject matter.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

FIG. 1 is a diagrammatic schematic view of an intraluminal imaging system 100, according to aspects of the present disclosure. The intraluminal imaging system 100 can be an intravascular ultrasound (IVUS) imaging system in some embodiments. The intraluminal imaging system 100 may include an intraluminal device 102, a patient interface module (PIM) 104, a console or processing system 106, a monitor 108, and an external imaging system 132 which may include angiography, ultrasound, X-ray, computed tomography (CT), MRI, or other imaging technologies, equipment, and methods. The intraluminal device 102 is sized and shaped, and/or otherwise structurally arranged to be positioned within a body lumen of a patient. For example, the intraluminal device 102 can be a catheter, guide wire, guide catheter, pressure wire, and/or flow wire in various embodiments. In some circumstances, the system 100 may include additional elements and/or may be implemented without one or more of the elements illustrated in FIG. 1. For example, the system 100 may omit one or both of the external ultrasound system 132 and the CT system 134.

The intraluminal imaging system 100 (or intravascular imaging system) can be any type of imaging system suitable for use in the lumens or vasculature of a patient. In some embodiments, the intraluminal imaging system 100 is an intraluminal ultrasound (IVUS) imaging system. In other embodiments, the intraluminal imaging system 100 may include systems configured for forward looking intraluminal ultrasound (FL-IVUS) imaging, intraluminal photoacoustic (IVPA) imaging, intracardiac echocardiography (ICE), transesophageal echocardiography (TEE), and/or other suitable imaging modalities.

It is understood that the system 100 and/or device 102 can be configured to obtain any suitable intraluminal imaging data. In some embodiments, the device 102 may include an imaging component of any suitable imaging modality, such as optical imaging, optical coherence tomography (OCT), etc. In some embodiments, the device 102 may include any suitable non-imaging component, including a pressure sensor, a flow sensor, a temperature sensor, an optical fiber, a reflector, a mirror, a prism, an ablation element, a radio frequency (RF) electrode, a conductor, and/or combinations thereof. Generally, the device 102 can include an imaging element to obtain intraluminal imaging data associated with the lumen 120. The device 102 may be sized and shaped (and/or configured) for insertion into a vessel or lumen 120 of the patient.

The system 100 may be deployed in a catheterization laboratory having a control room. The processing system 106 may be located in the control room. Optionally, the processing system 106 may be located elsewhere, such as in the catheterization laboratory itself. The catheterization laboratory may include a sterile field while its associated control room may or may not be sterile depending on the procedure to be performed and/or on the health care facility. The catheterization laboratory and control room may be used to perform any number of medical imaging procedures such as angiography, fluoroscopy, CT, IVUS, virtual histology (VH), forward looking IVUS (FL-IVUS), intraluminal photoacoustic (IVPA) imaging, a fractional flow reserve (FFR) determination, a coronary flow reserve (CFR) determination, optical coherence tomography (OCT), computed tomography, intracardiac echocardiography (ICE), forward-looking ICE (FLICE), intraluminal palpography, transesophageal ultrasound, fluoroscopy, and other medical imaging modalities, or combinations thereof. In some embodiments, device 102 may be controlled from a remote location such as the control room, such than an operator is not required to be in close proximity to the patient.

The intraluminal device 102, PIM 104, monitor 108, and external imaging system 132 may be communicatively coupled directly or indirectly to the processing system 106. These elements may be communicatively coupled to the medical processing system 106 via a wired connection such as a standard copper link or a fiber optic link and/or via wireless connections using IEEE 802.11 Wi-Fi standards, Ultra Wide-Band (UWB) standards, wireless FireWire, wireless USB, or another high-speed wireless networking standard. The processing system 106 may be communicatively coupled to one or more data networks, e.g., a TCP/IP-based local area network (LAN). In other embodiments, different protocols may be utilized such as Synchronous Optical Networking (SONET). In some cases, the processing system 106 may be communicatively coupled to a wide area network (WAN). The processing system 106 may utilize network connectivity to access various resources. For example, the processing system 106 may communicate with a Digital Imaging and Communications in Medicine (DICOM) system, a Picture Archiving and Communication System (PACS), and/or a Hospital Information System via a network connection.

At a high level, an ultrasound imaging intraluminal device 102 emits ultrasonic energy from a transducer array 124 included in scanner assembly 110 mounted near a distal end of the intraluminal device 102. The ultrasonic energy is reflected by tissue structures in the medium (such as a lumen 120) surrounding the scanner assembly 110, and the ultrasound echo signals are received by the transducer array 124. The scanner assembly 110 generates electrical signal(s) representative of the ultrasound echoes. The scanner assembly 110 can include one or more single ultrasound transducers and/or a transducer array 124 in any suitable configuration, such as a planar array, a curved array, a circumferential array, an annular array, etc. For example, the scanner assembly 110 can be a one-dimensional array or a two-dimensional array in some instances. In some instances, the scanner assembly 110 can be a rotational ultrasound device. The active area of the scanner assembly 110 can include one or more transducer materials and/or one or more segments of ultrasound elements (e.g., one or more rows, one or more columns, and/or one or more orientations) that can be uniformly or independently controlled and activated. The active area of the scanner assembly 110 can be patterned or structured in various basic or complex geometries. The scanner assembly 110 can be disposed in a side-looking orientation (e.g., ultrasonic energy emitted perpendicular and/or orthogonal to the longitudinal axis of the intraluminal device 102) and/or a forward-looking looking orientation (e.g., ultrasonic energy emitted parallel to and/or along the longitudinal axis). In some instances, the scanner assembly 110 is structurally arranged to emit and/or receive ultrasonic energy at an oblique angle relative to the longitudinal axis, in a proximal or distal direction. In some embodiments, ultrasonic energy emission can be electronically steered by selective triggering of one or more transducer elements of the scanner assembly 110.

The ultrasound transducer(s) of the scanner assembly 110 can be a piezoelectric micromachined ultrasound transducer (PMUT), capacitive micromachined ultrasonic transducer (CMUT), single crystal, lead zirconate titanate (PZT), PZT composite, other suitable transducer type, and/or combinations thereof. In an embodiment the ultrasound transducer array 124 can include any suitable number of individual transducer elements or acoustic elements between 1 acoustic element and 1000 acoustic elements, including values such as 2 acoustic elements, 4 acoustic elements, 36 acoustic elements, 64 acoustic elements, 128 acoustic elements, 500 acoustic elements, 812 acoustic elements, and/or other values both larger and smaller.

The PIM 104 transfers the received echo signals to the processing system 106 where the ultrasound image (including the flow information) is reconstructed and displayed on the monitor 108. The console or processing system 106 can include a processor and a memory. The processing system 106 may be operable to facilitate the features of the intraluminal imaging system 100 described herein. For example, the processor can execute computer readable instructions stored on the non-transitory tangible computer readable medium.

The PIM 104 facilitates communication of signals between the processing system 106 and the scanner assembly 110 included in the intraluminal device 102. This communication may include providing commands to integrated circuit controller chip(s) within the intraluminal device 102, select particular element(s) on the transducer array 124 to be used for transmit and receive, providing the transmit trigger signals to the integrated circuit controller chip(s) to activate the transmitter circuitry to generate an electrical pulse to excite the selected transducer array element(s), and/or accepting amplified echo signals received from the selected transducer array element(s) via amplifiers included on the integrated circuit controller chip(s). In some embodiments, the PIM 104 performs preliminary processing of the echo data prior to relaying the data to the processing system 106. In examples of such embodiments, the PIM 104 performs amplification, filtering, and/or aggregating of the data. In an embodiment, the PIM 104 also supplies high- and low-voltage DC power to support operation of the intraluminal device 102 including circuitry within the scanner assembly 110.

The processing system 106 receives echo data from the scanner assembly 110 by way of the PIM 104 and processes the data to reconstruct an image of the tissue structures in the medium surrounding the scanner assembly 110. Generally, the device 102 can be utilized within any suitable anatomy and/or body lumen of the patient. The processing system 106 outputs image data such that an image of the vessel or lumen 120, such as a cross-sectional IVUS image of the lumen 120, is displayed on the monitor 108. Lumen 120 may represent fluid filled or surrounded structures, both natural and man-made. Lumen 120 may be within a body of a patient. Lumen 120 may be a blood vessel, as an artery or a vein of a patient's vascular system, including cardiac vasculature, peripheral vasculature, neural vasculature, renal vasculature, and/or or any other suitable lumen inside the body. For example, the device 102 may be used to examine any number of anatomical locations and tissue types, including without limitation, organs including the liver, heart, kidneys, gall bladder, pancreas, lungs; ducts; intestines; nervous system structures including the brain, dural sac, spinal cord and peripheral nerves; the urinary tract; as well as valves within the blood, chambers or other parts of the heart, and/or other systems of the body. In addition to natural structures, the device 102 may be used to examine man-made structures such as, but without limitation, heart valves, stents, shunts, filters and other devices.

The controller or processing system 106 may include a processing circuit having one or more processors in communication with memory and/or other suitable tangible computer readable storage media. The controller or processing system 106 may be configured to carry out one or more aspects of the present disclosure. In some embodiments, the processing system 106 and the monitor 108 are separate components. In other embodiments, the processing system 106 and the monitor 108 are integrated in a single component. For example, the system 100 can include a touch screen device, including a housing having a touch screen display and a processor. The system 100 can include any suitable input device, such as a touch sensitive pad or touch screen display, keyboard/mouse, joystick, button, etc., for a user to select options shown on the monitor 108. The processing system 106, the monitor 108, the input device, and/or combinations thereof can be referenced as a controller of the system 100. The controller can be in communication with the device 102, the PIM 104, the processing system 106, the monitor 108, the input device, and/or other components of the system 100.

In some embodiments, the intraluminal device 102 includes some features similar to traditional solid-state IVUS catheters, such as the EagleEye® catheter available from Volcano Corporation and those disclosed in U.S. Pat. No. 7,846,101 hereby incorporated by reference in its entirety. For example, the intraluminal device 102 may include the scanner assembly 110 near a distal end of the intraluminal device 102 and a transmission line bundle 112 extending along the longitudinal body of the intraluminal device 102. The cable or transmission line bundle 112 can include a plurality of conductors, including one, two, three, four, five, six, seven, or more conductors.

The transmission line bundle 112 terminates in a PIM connector 114 at a proximal end of the intraluminal device 102. The PIM connector 114 electrically couples the transmission line bundle 112 to the PIM 104 and physically couples the intraluminal device 102 to the PIM 104. In an embodiment, the intraluminal device 102 further includes a guidewire exit port 116. Accordingly, in some instances the intraluminal device 102 is a rapid-exchange catheter. The guidewire exit port 116 allows a guidewire 118 to be inserted towards the distal end in order to direct the intraluminal device 102 through the lumen 120.

The monitor 108 may be a display device such as a computer monitor or other type of screen. The monitor 108 may be used to display selectable prompts, instructions, and visualizations of imaging data to a user. In some embodiments, the monitor 108 may be used to provide a procedure-specific workflow to a user to complete an intraluminal imaging procedure. This workflow may include performing a pre-stent plan to determine the state of a lumen and potential for a stent, as well as checking on a stent that has been positioned in a lumen. The workflow may be presented to a user as any of the displays or visualizations shown in FIGS. 5-12.

The external imaging system 132 can be configured to obtain x-ray, radiographic, angiographic/venographic (e.g., with contrast), and/or fluoroscopic (e.g., without contrast) images of the body of patient (including the vessel 120). External imaging system 132 may also be configured to obtain computed tomography images of the body of patient (including the vessel 120). The external imaging system 132 may include an external ultrasound probe configured to obtain ultrasound images of the body of the patient (including the vessel 120) while positioned outside the body. In some embodiments, the system 100 includes other imaging modality systems (e.g., MRI) to obtain images of the body of the patient (including the vessel 120). The processing system 106 can utilize the images of the body of the patient in conjunction with the intraluminal images obtained by the intraluminal device 102.

Figure 2:
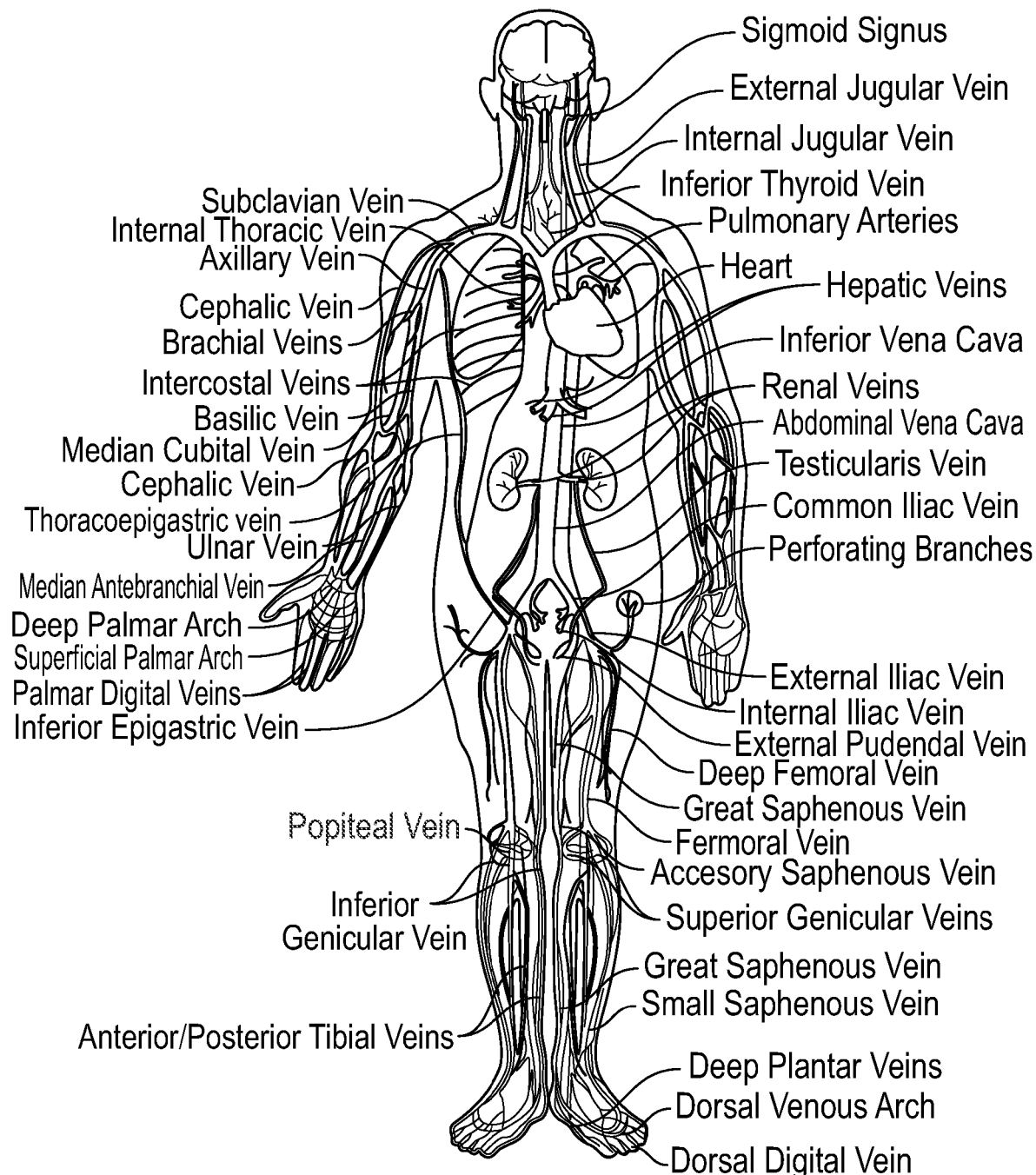
FIG. 2 illustrates blood vessels (e.g., arteries and veins) in the human body.

FIG. 2 illustrates blood vessels (e.g., arteries and veins) in the human body. For example, veins of the human body are labeled. Aspects of the present disclosure can be related to peripheral vasculature, e.g., veins in the torso or legs.

Occlusions can occur in arteries or veins. An occlusion can be generally representative of any blockage or other structural arrangement that results in a restriction to the flow of fluid through the lumen (e.g., an artery or a vein), for example, in a manner that is deleterious to the health of the patient. For example, the occlusion narrows the lumen such that the cross-sectional area of the lumen and/or the available space for fluid to flow through the lumen is decreased. Where the anatomy is a blood vessel, the occlusion may be a result of narrowing due to compression (e.g., from external vessels), plaque buildup, including without limitation plaque components such as fibrous, fibro-lipidic (fibro fatty), necrotic core, calcified (dense calcium), blood, and/or different stages of thrombus (acute, sub-acute, chronic, etc.). In some instances, the occlusion can be referenced as thrombus, a stenosis, and/or a lesion. Generally, the composition of the occlusion will depend on the type of anatomy being evaluated. Healthier portions of the anatomy may have a uniform or symmetrical profile (e.g., a cylindrical profile with a circular cross-sectional profile). The occlusion may not have a uniform or symmetrical profile. Accordingly, diseased or compressed portions of the anatomy, with the occlusion, will have a non-symmetric and/or otherwise irregular profile. The anatomy can have one occlusion or multiple occlusions.

Build-up of occlusion (e.g., thrombus, deep vein thrombosis or DVT, chronic total occlusion or CTO, etc.) is one way in which the cross-sectional area of the vein in the peripheral vasculature (e.g., torso, abdomen, groin, leg) may be reduced. Other anatomy that contacts the vein can also reduce its cross-sectional area, thereby restricting blood flow therethrough. For example, arteries or ligaments in the torso, abdomen, groin, or leg can press against a vein, which changes the shape of the vein and reduces its cross-sectional area. Such reductions in cross-sectional area resulting from contact with other anatomy can be referenced as compression, in that the walls of the vein are compressed as a result of the contact with the artery or ligament.

Figure 3:
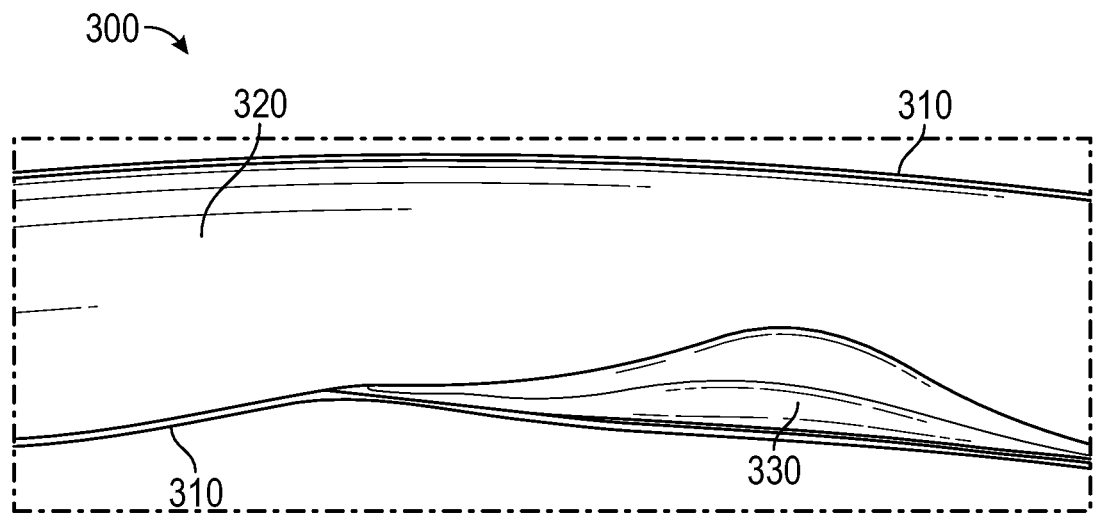
FIG. 3 illustrates a blood vessel incorporating a thrombus.

FIG. 3 illustrates a blood vessel 300 incorporating a thrombus 330. The thrombus occurs between the vessel walls 310 and may restrict the flow of blood 320. Thrombuses come in many types, including sub-acute thrombus, acute thrombus, and chronic thrombus.

Figure 4:
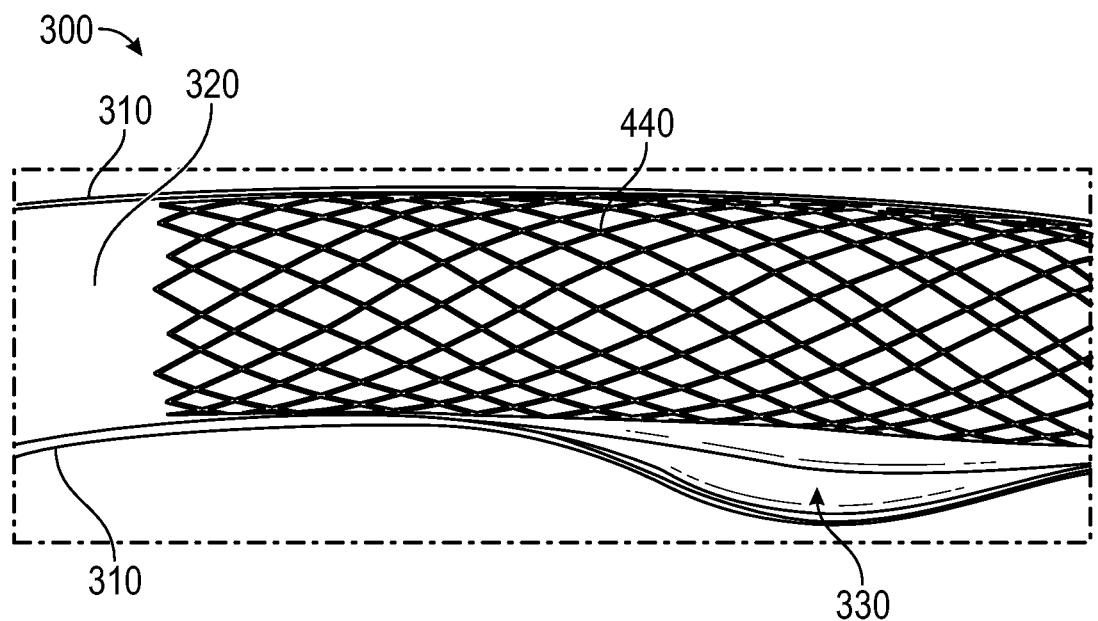
FIG. 4 illustrates a blood vessel incorporating a thrombus and with a stent expanded inside it to restore flow.

FIG. 4 illustrates a blood vessel 300 incorporating a thrombus 330 and with a stent 440 expanded inside it to restore flow. The stent 440 compresses and arrests the thrombus 330, preventing the thrombus 330 from traveling through the blood vessel 300. The stent 440 also pushes the vessel walls 310 outward, thus reducing the flow restriction for the blood 320.

Figure 5:
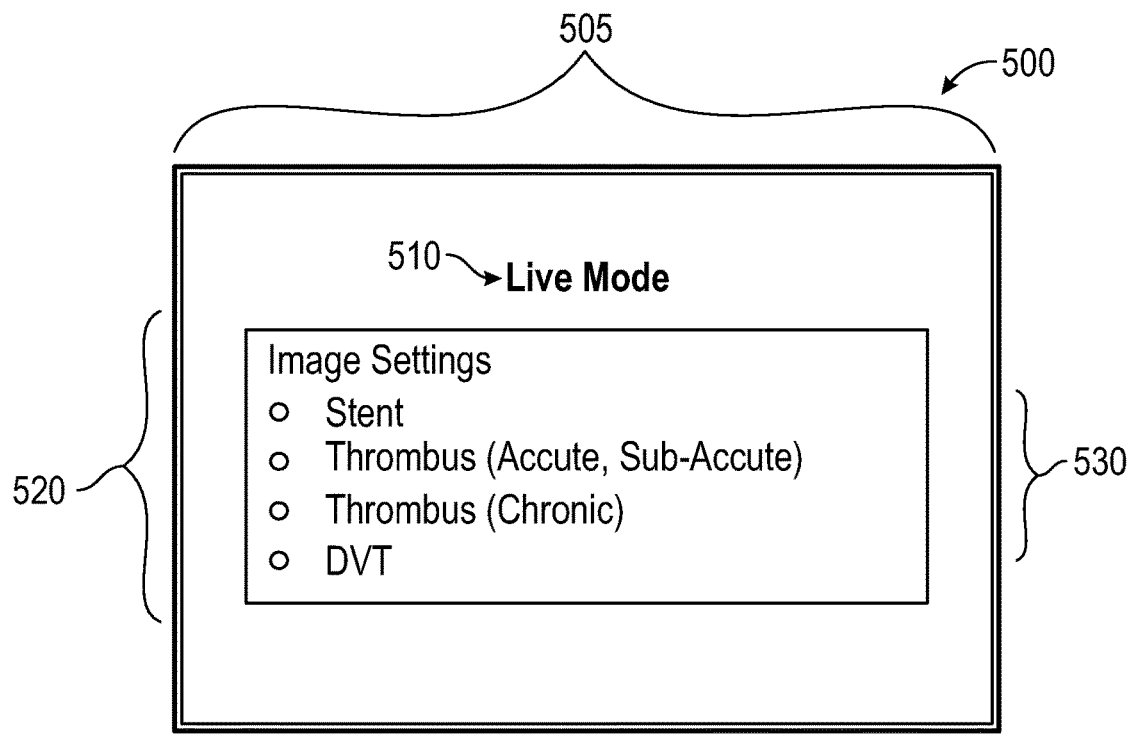
FIG. 5 illustrates a screen display related to image adjustment according to aspects of the present disclosure.

FIG. 5 illustrates a screen display related to image adjustment according to aspects of the present disclosure. Exemplary screen displays or graphical user interfaces (GUIs can be shown on a display of the case-specific imaging presets system 500, for example, a display of a console, a cart, a bedside controller, a mobile device (e.g., smartphone, tablet, personal digital assistant or PDA), a laptop computer, a desktop computer, etc. The display may be a touchscreen display, and may be in communication with a computer with a processing circuit (e.g., one or more processors and memory). The processing circuit can generate and output the display data to cause the display to show the screen displays of FIGS. 5-6. The computer, processing circuit, and/or processor may also be in communication with a user interface on which user provides inputs. The inputs can be selections of items on the screen displays. The user interface can be a touchscreen display in some instances, or may incorporate a keyboard, a mouse, trackball, stylus, a video-game-style controller with buttons and a joystick, etc.

The imaging presets system display 505 includes a mode indicator 510, an image settings presets menu or image type selection menu 520, and image settings presets 530. In the example shown in FIG. 5, the mode indicator 510 shows that the system is in "Live" mode. Other possible modes may include but are not limited to "Review", "Playback", "Record" "Pullback", and "Standby". As shown in the imaging presets system display 505 of FIG. 5, the image adjustment can be based on the user-selectable imaging setting presets 530 selected from the preset menu 520. In this example, possible image setting presets include "Stent" "Thrombus (acute, sub-accute)", "Thrombus (chronic)", and "DVT" (deep-vein thrombosis). These presets represent different diseases or structures for the case-specific imaging presets system 500 to image, and in FIG. 5 they are specifically diseases or objects of the venous system, although case-specific imaging presets system 500 may be employed to image other disease types (e.g., compression), other object types (e.g., guidewires), or other anatomical systems (e.g., arterial, lymphatic, coronary).

The imaging settings presets 530 control how the IVUS images are displayed. The screen display allows the user to choose image presets for certain disease types or treatment device types. Having the preset image settings allow the user to view certain disease types or treatment device types more clearly. For example, the respective settings can enhance the display of IVUS images in a manner that highlights (e.g., renders more visible or distinguishable) the features of the corresponding disease type or treatment device type. The screen display provides easy options for the user to choose from. The present options can be provided for a live mode (e.g., while the IVUS data is being collected) or a playback mode (after IVUS data has been collected).

Figure 6:
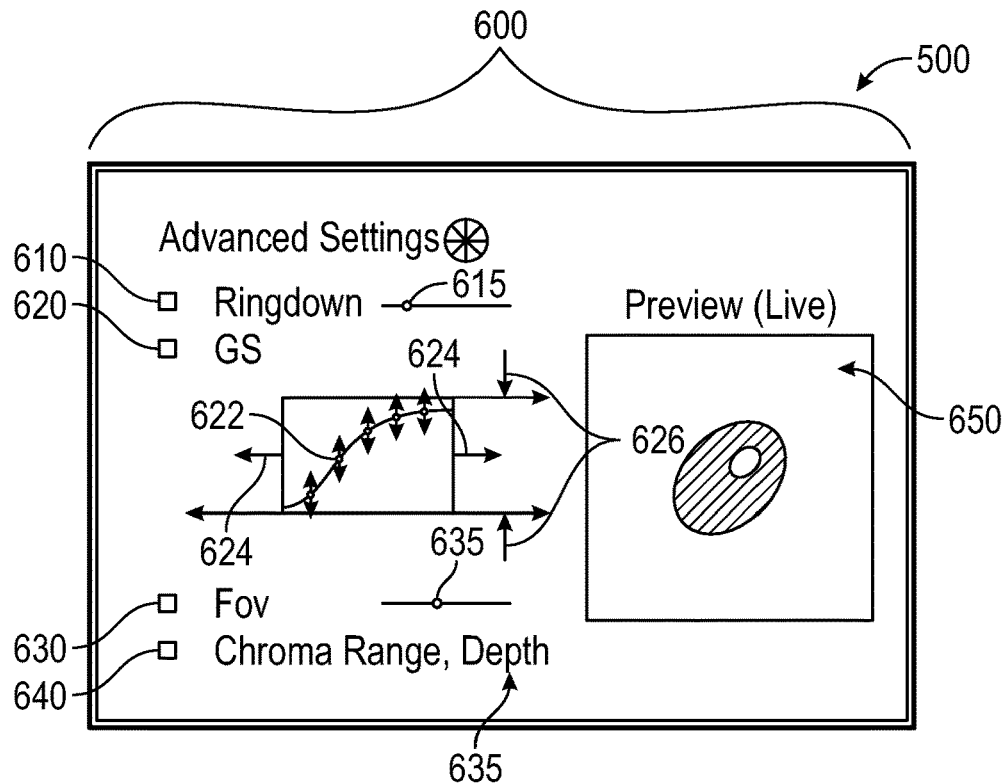
FIG. 6 illustrates a screen display with advanced settings that provide the user more control over how images are displayed, according to aspects of the present disclosure.

FIG. 6 illustrates a screen display with advanced settings 600 that provide the user more control over how images are displayed, according to aspects of the present disclosure. The image settings can include a ringdown setting 610, gain curve 620, field of view (FOV) setting 630, blood flow detection, chroma 640 (range, depth), etc. The user-adjustable settings can be provided in the form of a slider bar, graph with sliders, on/off, numerical value, etc. A live preview pane 650 of the IVUS image is provided adjacent to the settings. For example, the live preview IVUS image reflects the settings in real-time or near real-time so that the user can see how the changes in settings affect the display of the IVUS image. In this manner, the screen display provides the user a view of how the IVUS image will be displayed while the settings adjustments are being made. In some embodiments, two IVUS images are displayed adjacent to the settings, e.g., one IVUS image that stays with the current settings and one IVUS image that dynamically changes with the new settings. In this manner, the user can compare the difference the settings make on the IVUS images side-by-side.

According to embodiments of the present disclosure, selection of an image setting preset 530 automatically selects preset or default values for one or more of the advanced settings 600. In some embodiments, selection of an image setting preset 530 automatically selects default values for all of the advanced settings. However, it may still be possible for the user to enter the advanced settings screen 600 and make manual alterations to the default settings. In some embodiments, it may be possible for the user to alter the settings 600 in the advanced settings screen and then save the results as a new settings preset 530 with a new name (e.g., "Stent, polymer coated").

In the example shown in FIG. 5, the ringdown setting 610 can be selected with a slider 615, indicating the number of frames the system is looking back in time. In this example, setting the slider to the leftmost end indicates no ringdown subtraction, whereas setting it to the rightmost end may indicate the subtraction of ringdown echoes as far as five frames back. In the same example, the gain curve 620 can be selected with 5 movable data points 622 which can be arranged upward or downward in a manner similar to a graphic equalizer for a sound system. The gain curve 620 may also be altered with horizontal range expanders 624 and vertical range expanders 626. In the same example, the field of view 630 can be adjusted with a slider 635, such that for example the leftmost position of the slider indicates the minimum possible FOV for the imaging sensor (e.g., 30 degrees), whereas the rightmost position of the slider indicates the maximum possible FOV of the imaging sensor (e.g., 360 degrees). In the same example, the chroma selection 640 may adjust two different parameters 645: range/depth (the distance at which blood flow color coding may occur) and sensitivity (the amount of movement required to produce a color change, e.g., dark red for slower moving, bright red for faster moving). Other types of chroma adjustments are possible and may be employed instead or in addition to these.

In other embodiments, other or additional parameters may also be adjustable than those shown here, including but not limited to blood flow detection, brightness, contrast, saturation, sharpness, hue, and tint. As these parameters 600 are adjusted as described above, the image in the preview pane 650 will change to demonstrate the effect of the new settings. For example, by changing the level of ringdown subtraction 610, a user may alter the amount of ringdown subtraction that occurs, either increasing it to eliminate image artifacts, or decreasing it to enhance or otherwise improve the appearance, visibility, distinguishability, or texture of faint tissue details. These effects can be seen in the preview pane 650 without the user having to exit from the advanced settings screen. In some embodiments, a cancel function may also be available to permit the user to revert to the preset values.

Figure 7A:
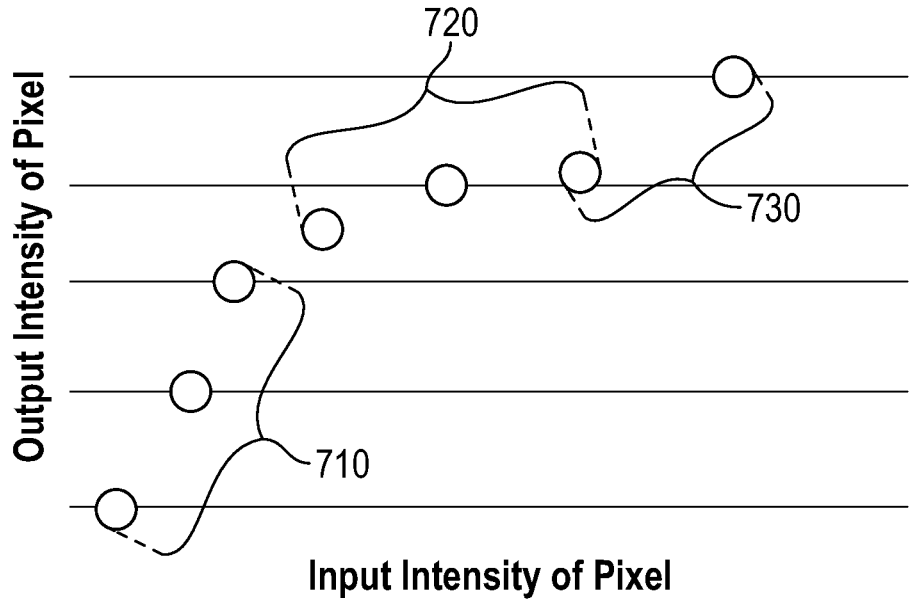
FIG. 7a illustrates an example baseline image gain curve for imaging a thrombus within a blood vessel, in accordance with aspects of the present disclosure.

FIG. 7a illustrates an example baseline image gain curve for imaging a thrombus 330 within a blood vessel 300, in accordance with aspects of the present disclosure. The X-axis represents the input intensity of a pixel (i.e., the intensity of the raw data point received by the case-specific imaging presets system 500), whereas the Y-axis represents the output intensity of the same pixel in a real-time processed image. With zero image processing, the output intensity may be equal to the input intensity for all intensities, or else linearly related to the input intensity.

A thrombus 330 is a blood clot composed predominantly of blood cells, and is generally of higher density than the blood medium 320 surrounding it, but of lower density than the vessel walls 310 surrounding both the thrombus 330 and the blood medium 320. Therefore, in order to obtain a clear image of a thrombus 330, it may be desirable to have a high gain (and thus a high contrast) for low input intensities, as represented by the steep slope in region 710, and a relatively flat gain curve (i.e., constant or near-constant output intensity regardless of input intensity) in region 720, and a steeper curve again in region 730 for higher input intensities. This may help distinguish low-intensity (i.e., low-brightness or low-density) features of the thrombus 330 from the surrounding blood medium 320, and to distinguish both thrombus 330 and blood 320 from the higher-intensity (i.e., higher-brightness or higher-density) features of the surrounding vessel walls 310, while smoothing out minor differences in features of intermediate density, which may be less relevant for the analysis of a thrombus 330.

The gain curve shown in FIG. 7a may be suitable for a relatively immature plaque with low density. A person of ordinary skill in the art will appreciate that a different gain curve (e.g., less steep in regions 710 and 730, and less flat in region 720) may be more suitable for imaging a mature plaque that incorporates higher-density features such as webbing/scarring or a necrotic core. With existing systems, such gain curves must be assembled by the user on a case-by-case basis. The present disclosure both saves time and effort and also improves image quality, by selecting a preset gain curve that is optimized for the feature types to be examined.

Figure 7B:
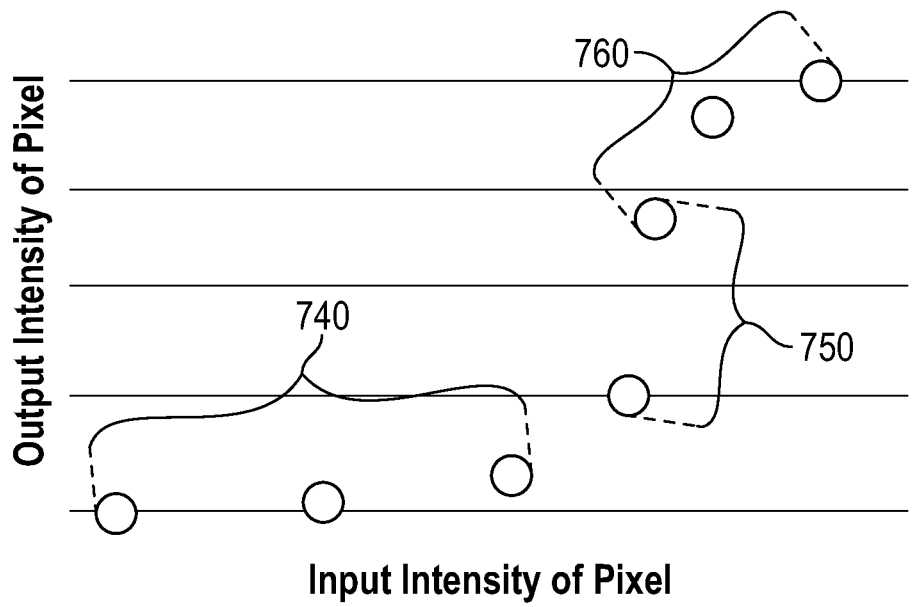
FIG. 7b illustrates an example baseline image gain curve for imaging a stent within a blood vessel, in accordance with aspects of the present disclosure.

FIG. 7b illustrates an example baseline image gain curve for imaging a stent 440 within a blood vessel 300, in accordance with aspects of the present disclosure. As with FIG. 8a, The X-axis represents the input intensity of a pixel (i.e., the intensity of the raw data point received by the case-specific imaging presets system 500), whereas the Y-axis represents the output intensity of the same pixel in a real-time processed image.

The gain curve of FIG. 7b is relatively flat (e.g., has a small slope) in region 740, steep (large slope) in region 750, and slightly less steep (moderate slope) in region 760. This may tend to allow the features and margins of a stent 440 to be brightly visible in the image, while clearly distinguishing it from the surrounding vessel 300. This gain curve may be less suitable for distinguishing detailed features of a thrombus 330 or other vessel disease.

In an example, a gain curve comprises points, and editing the gain curve is accomplished by selecting and moving the points, thereby adjusting the magnitude and slope of the curve in different regions.

Figure 8:
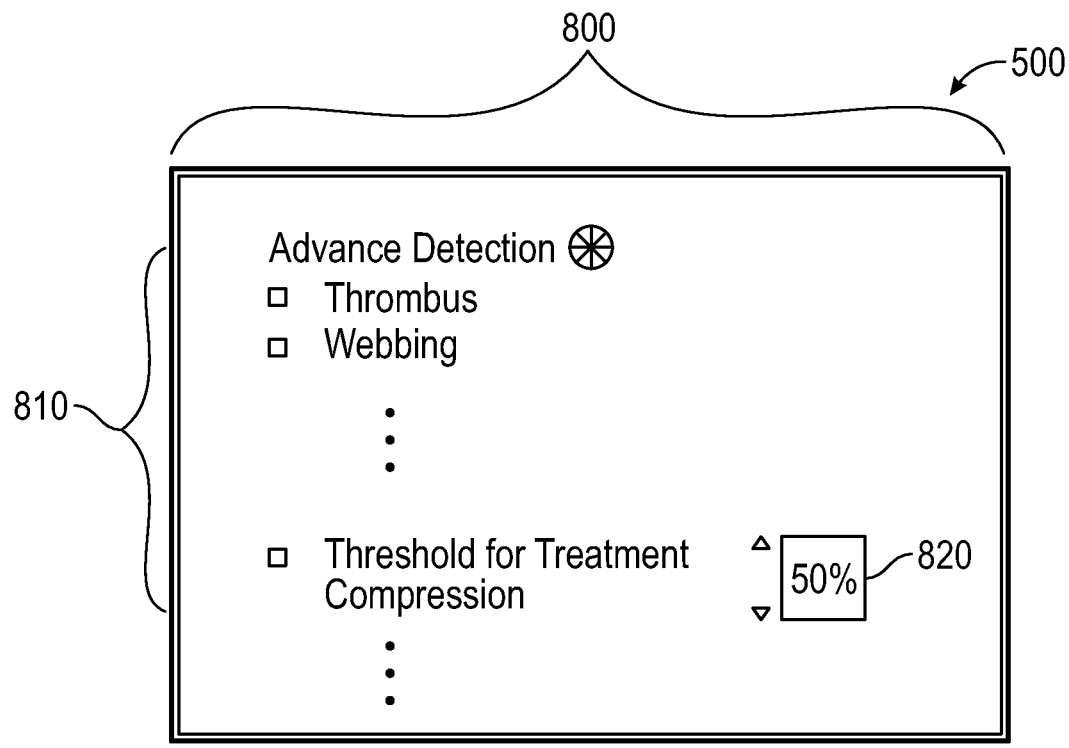
FIG. 8 illustrates an advance detection screen display that allows a user to switch on or off advanced/automated detection of anatomical features or other automated thresholds, in accordance with aspects of the present disclosure.

FIG. 8 illustrates an advance detection screen display 800 that allows a user to switch on or off advanced/automated detection of anatomical features or other automated thresholds 810, in accordance with aspects of the present disclosure. This user-selectable advance detection feature can provide a user with optimized understanding of the anatomy being shown in an image (e.g., an intravenous IVUS image). For example, anatomical features such as thrombus or webbing can be automatically identified with the automated detection turned on. The IVUS image can be displayed in a manner that visually accentuates the detected anatomical features, such as by coloring, shading, highlighting, text labels, numerical labels, etc. Display of the IVUS image can also be based on thresholds. For example, a degree of compression of the vein can provide a user guidance on whether to treat the vein. The advance detection screen display 800 may allow the user to input/change the particular threshold value (e.g., 50% compression or other occlusion). For example, clickable arrows can be provided on the display to increase or decrease the threshold value, and/or the numerical value can be input into the threshold value field, or other input methods may be employed. The IVUS image can be displayed in a manner that calls attention to the threshold being crossed, such as by coloring, shading, highlighting, text labels, numerical labels, etc.

Figure 9:
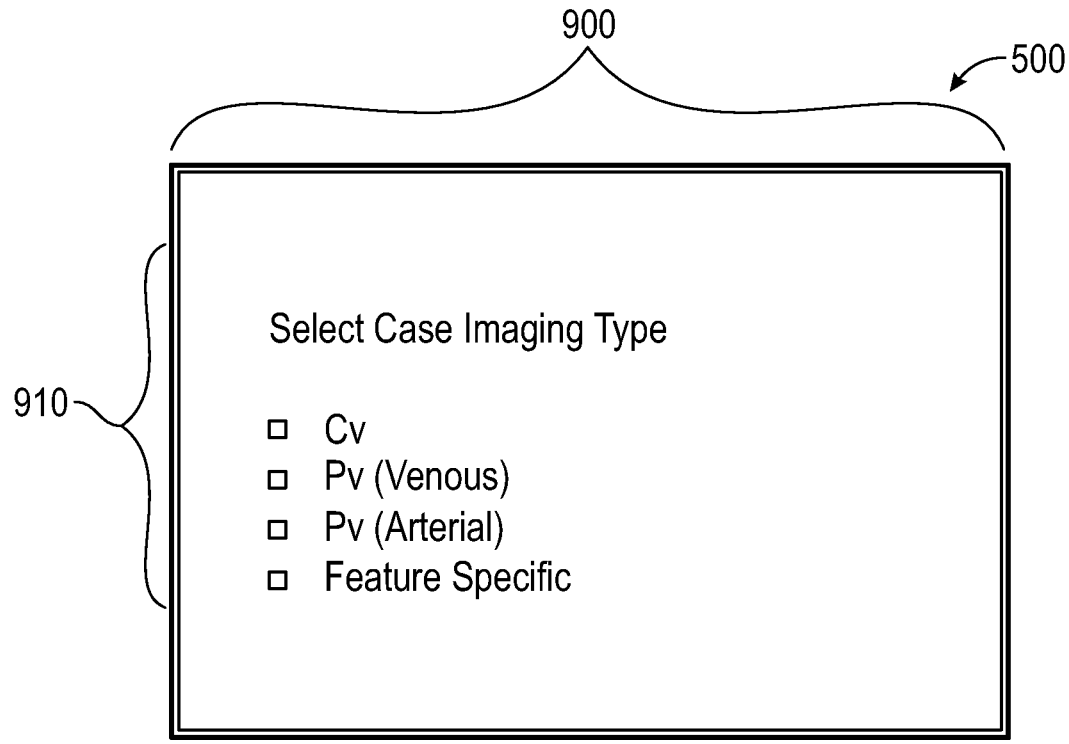
FIG. 9 illustrates an example welcome screen for the case-specific imaging presets system.

FIG. 9 illustrates an example welcome screen 900 for the case-specific imaging presets system 500. Similar to the imaging presets system display 505 shown in FIG. 5, the user can select between procedure types via a procedure type selection menu or image type selection menu 910. In this example, the available options are coronary vascular or vasculature (Cv) imaging, peripheral vascular or vasculature (Pv) venous imaging, or Pv arterial imaging. Each different type of case offers the user different procedure type specific modalities and algorithms. A "Feature Specific" option may deliver the user to a different selection screen such as display 505 or 800. In other embodiments, different imaging types or procedure types may be available for selection.

Figure 10:
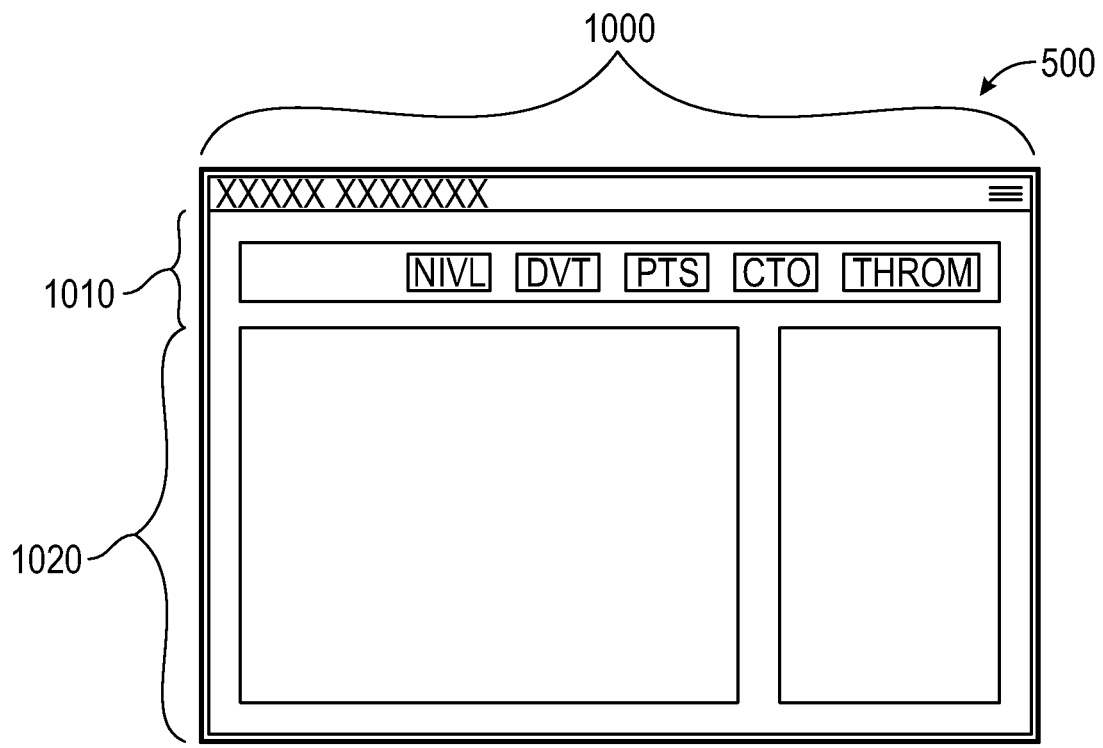
FIG. 10 illustrates a screen display that allows a user to select a particular type of vascular imaging for the patient case, in accordance with aspects of the present disclosure.

FIG. 10 illustrates a screen display 1000 that allows a user to select a particular type of vascular imaging through an image type selection menu 1010 for the patient case, in accordance with aspects of the present disclosure. This example illustrates a screen display after the Pv venous case type is selected in welcome screen 900. The case log 1020 shown in FIG. 10 provides the user IVUS modes (case types) that are specific to Pv venous (e.g., disease types such as compression, non-thrombotic iliac vein lesion or NIVL, deep vein thrombosis or DVT, post-thrombotic syndrome or PTS, or chronic total occlusion or CTO). Some embodiments may also include access to external imaging from an external imaging system 132, to thrombectomy software applications for treatment with a thrombectomy device, etc. The different IVUS modes can include disease-specific imaging presets, types of measurements, user instructions, etc. In this manner, the user can select disease type and/or types of measurements for IVUS imaging, each of which will trigger its own set of preset or default values for the image processing parameters 600.

In other embodiments, the system is configured to select image types associated with coronary and arterial diseases, including but not limited to plaque or lesions.

Figure 11:
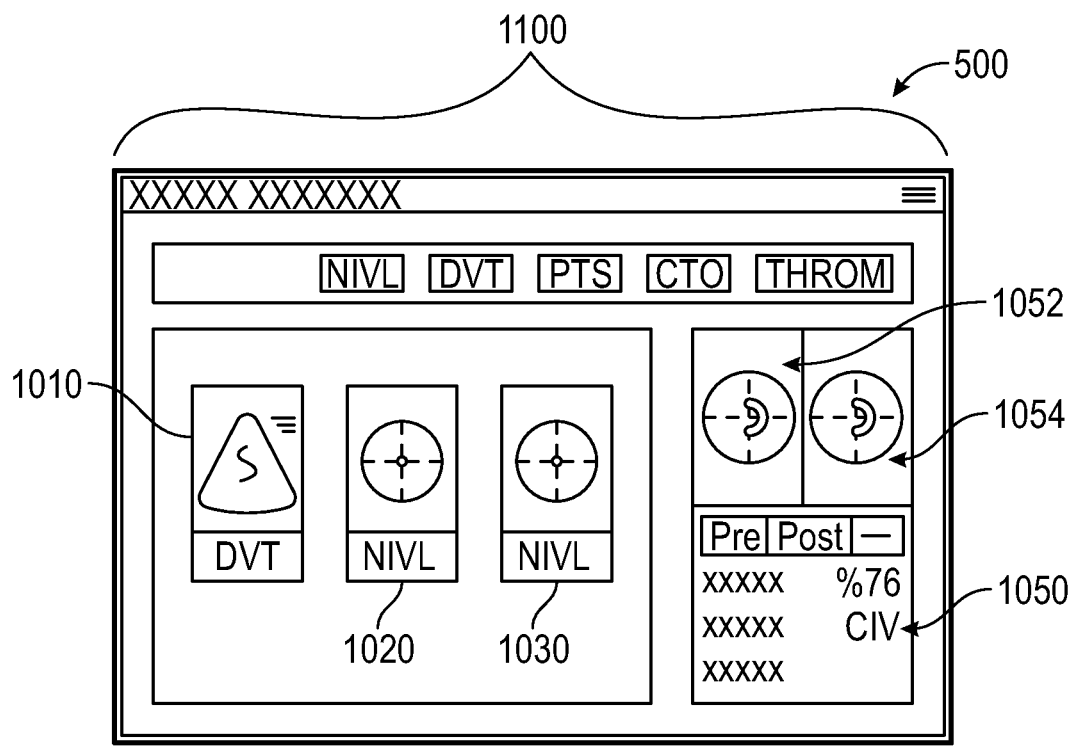
FIG. 11 illustrates a screen display after three imaging procedures have been performed, in accordance with aspects of the present disclosure.

FIG. 11 illustrates a screen display 1100 after three imaging procedures have been performed: one DVT procedure 1010 and two NIVL IVUS procedures 1020 and 1030, in accordance with aspects of the present disclosure. For example, the IVUS procedure can be a pullback in which the imaging data is obtained while the ultrasound catheter is moved longitudinally within the vessel (e.g., from a distal location where the left and right common iliac veins branch off from the inferior vena cava to a more proximal location farther from the branch). The selected IVUS case (the second case 1020 of the three cases 1010, 1020, and 1030) can be highlighted. As shown on the right side of the image, a report section 1050 of the GUI allows the user to easily annotate the selected imaging procedure as pre-treatment or post-treatment (e.g., pre-stent or post-stent). Exemplary IVUS frames 1052 and 1054 (e.g., bookmarked frames, frames representative of the occlusion, proximal/distal edges of the lesion, proximal/distal landing zones, proximal/distal reference points, etc.) from the selected imaging procedure 1020 are displayed in the report section 1050. Additional information about the imaging procedure, such as the name of the vessel, percentage of compression, percentage of occlusion, etc., may also be displayed. The GUI also allows the user to mark (e.g., the heart symbol) the imaging procedure as a favorite, such as for archiving. In this example, cases 1020 and 1030 have been favorited and are identified by the heart symbols (the upper right corner of the second and third cases). Other identifiers may be used in addition or instead.

Figure 12:
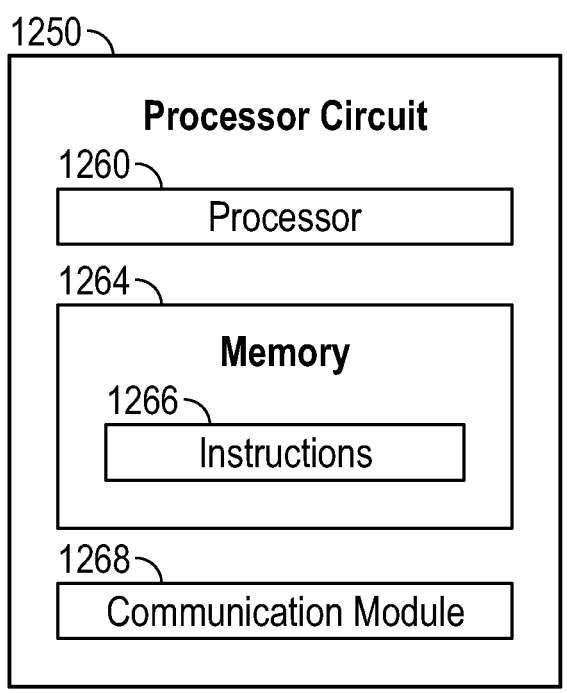
FIG. 12 is a schematic diagram of a processor circuit, according to embodiments of the present disclosure.

FIG. 12 is a schematic diagram of a processor circuit 1250, according to embodiments of the present disclosure. The processor circuit 1250 may be implemented in the ultrasound imaging system 100, or other devices or workstations (e.g., third-party workstations, network routers, etc.), or on a cloud processor or other remote processing unit, as necessary to implement the method. As shown, the processor circuit 1250 may include a processor 1260, a memory 1264, and a communication module 1268. These elements may be in direct or indirect communication with each other, for example via one or more buses.

The processor 1260 may include a central processing unit (CPU), a digital signal processor (DSP), an ASIC, a controller, or any combination of general-purpose computing devices, reduced instruction set computing (RISC) devices, application-specific integrated circuits (ASICs), field programmable gate arrays (FPGAs), or other related logic devices, including mechanical and quantum computers. The processor 1260 may also comprise another hardware device, a firmware device, or any combination thereof configured to perform the operations described herein. The processor 1260 may also be implemented as a combination of computing devices, e.g., a combination of a DSP and a microprocessor, a plurality of microprocessors, one or more microprocessors in conjunction with a DSP core, or any other such configuration.

The memory 1264 may include a cache memory (e.g., a cache memory of the processor 1260), random access memory (RAM), magnetoresistive RAM (MRAM), read-only memory (ROM), programmable read-only memory (PROM), erasable programmable read only memory (EPROM), electrically erasable programmable read only memory (EEPROM), flash memory, solid state memory device, hard disk drives, other forms of volatile and non-volatile memory, or a combination of different types of memory. In an embodiment, the memory 1264 includes a non-transitory computer-readable medium. The memory 1264 may store instructions 1266. The instructions 1266 may include instructions that, when executed by the processor 1260, cause the processor 1260 to perform the operations described herein. Instructions 1266 may also be referred to as code. The terms "instructions" and "code" should be interpreted broadly to include any type of computer-readable statement(s). For example, the terms "instructions" and "code" may refer to one or more programs, routines, subroutines, functions, procedures, etc. "Instructions" and "code" may include a single computer-readable statement or many computer-readable statements.

The communication module 1268 can include any electronic circuitry and/or logic circuitry to facilitate direct or indirect communication of data between the processor circuit 1250, and other processors or devices. In that regard, the communication module 1268 can be an input/output (I/O) device. In some instances, the communication module 1268 facilitates direct or indirect communication between various elements of the processor circuit 1250 and/or the ultrasound imaging system 100. The communication module 1268 may communicate within the processor circuit 1250 through numerous methods or protocols. Serial communication protocols may include but are not limited to US SPI, I$^2$C, RS-232, RS-485, CAN, Ethernet, ARINC 429, MODBUS, MIL-STD-1553, or any other suitable method or protocol. Parallel protocols include but are not limited to ISA, ATA, SCSI, PCI, IEEE-488, IEEE-1284, and other suitable protocols. Where appropriate, serial and parallel communications may be bridged by a UART, USART, or other appropriate subsystem.

External communication (including but not limited to software updates, firmware updates, preset sharing between the processor and central server, or readings from the ultrasound device) may be accomplished using any suitable wireless or wired communication technology, such as a cable interface such as a USB, micro USB, Lightning, or FireWire interface, Bluetooth, Wi-Fi, ZigBee, Li-Fi, or cellular data connections such as 2G/GSM, 3G/UMTS, 4G/LTE/WiMax, or 5G. For example, a Bluetooth Low Energy (BLE) radio can be used to establish connectivity with a cloud service, for transmission of data, and for receipt of software patches. The controller may be configured to communicate with a remote server, or a local device such as a laptop, tablet, or handheld device, or may include a display capable of showing status variables and other information. Information may also be transferred on physical media such as a USB flash drive or memory stick.

A number of variations are possible on the examples and embodiments described above. For example, the case-specific imaging presets system may be employed in anatomical systems within the body other than those described, or may define image enhancement presets for other disease types, object types, or procedure types than those described. The technology described herein may be applied to intraluminal imaging sensors of diverse types, whether currently in existence or hereinafter developed.

Accordingly, the logical operations making up the embodiments of the technology described herein are referred to variously as operations, steps, objects, elements, components, or modules. Furthermore, it should be understood that these may be performed in any order, unless explicitly claimed otherwise or a specific order is inherently necessitated by the claim language. All directional references e.g., upper, lower, inner, outer, upward, downward, left, right, lateral, front, back, top, bottom, above, below, vertical, horizontal, clockwise, counterclockwise, proximal, and distal are only used for identification purposes to aid the reader's understanding of the claimed subject matter, and do not create limitations, particularly as to the position, orientation, or use of the case-specific imaging presets system. Connection references, e.g., attached, coupled, connected, and joined are to be construed broadly and may include intermediate members between a collection of elements and relative movement between elements unless otherwise indicated. As such, connection references do not necessarily imply that two elements are directly connected and in fixed relation to each other. The term "or" shall be interpreted to mean "and/or" rather than "exclusive or." Unless otherwise noted in the claims, stated values shall be interpreted as illustrative only and shall not be taken to be limiting.

The above specification, examples and data provide a complete description of the structure and use of exemplary embodiments of the case-specific imaging presets system as defined in the claims. Although various embodiments of the claimed subject matter have been described above with a certain degree of particularity, or with reference to one or more individual embodiments, those skilled in the art could make numerous alterations to the disclosed embodiments without departing from the spirit or scope of the claimed subject matter. Still other embodiments are contemplated. It is intended that all matter contained in the above description and shown in the accompanying drawings shall be interpreted as illustrative only of particular embodiments and not limiting. Changes in detail or structure may be made without departing from the basic elements of the subject matter as defined in the following claims.

What is claimed is:

1. An intraluminal ultrasound imaging system, comprising:
   a processor circuit configured for communication with an intraluminal ultrasound imaging catheter, a display, and a user interface, wherein the processor circuit is configured to:
   receive, via the user interface, a selection of a thrombus option or a stent option from a plurality of image type options, wherein the plurality of image type options comprises:
      the thrombus option, wherein the thrombus option is associated with a gain curve comprising a first preset non-linear shape specific to the thrombus option; and
      the stent option, wherein the stent option is associated with the gain curve comprising a second preset non-linear shape specific to the stent option;
   identify the gain curve based on the selection such that the gain curve comprises;
      the first preset non-linear shape specific to the thrombus option when the selection is of the thrombus option; or
      the second preset non-linear shape specific to the stent option when the selection is of the stent option,
      wherein the gain curve determines a visual aspect of how an intraluminal ultrasound image is displayed on the display; and
   output, to the display, a visual representation of the gain curve with the first preset non-linear shape or the second preset non-linear shape,
   wherein the visual representation of the gain curve comprises:
      a first axis comprising a plurality of values of an input intensity of a pixel;
      a second axis comprising a plurality of values of an output intensity of the pixel; and
      a plurality of data points along the first preset non-linear shape or the second preset non-linear shape,
   wherein the plurality of data points is configured to be movable by a user to change:
      a curvature of the gain curve from the first preset non-linear shape or the second preset non-linear shape to a user-defined shape; and
      the visual aspect of how the intraluminal ultrasound image is displayed on the display,
   wherein the processor circuit is configured to receive the intraluminal ultrasound image obtained by the intraluminal ultrasound imaging catheter while the intraluminal ultrasound imaging catheter is positioned within a patient, wherein the processor circuit is configured to output, to the display, the intraluminal ultrasound image such that the intraluminal ultrasound image is displayed according to the visual aspect.

2. The system of claim 1,
wherein the intraluminal ultrasound image comprises a stent, and
wherein, when the selection is of the stent option, the processor circuit is configured to output the intraluminal ultrasound image such that the stent in the intraluminal ultrasound image is enhanced.

3. The system of claim 1,
wherein the intraluminal ultrasound image comprises a thrombus, and
wherein the processor circuit is configured to output the intraluminal ultrasound image such that the thrombus in the intraluminal ultrasound image is enhanced.

4. The system of claim 1,
wherein the processor circuit is configured to output, to the display, a detection option associated with an anatomical feature,
wherein the anatomical feature comprises at least one of a thrombus or a webbing,
wherein, in response to the processor circuit receiving a selection of the detection option, the processor circuit is configured to identify the anatomical feature in the intraluminal ultrasound image.

5. The system of claim 1,
wherein the processor circuit is further configured to change at least one of ringdown, contrast, saturation, hue, field of view, or chroma, based on the selection.

6. The system of claim 1, further comprising:
the intraluminal ultrasound imaging catheter.

7. The system of claim 3,
wherein the thrombus comprises at least one of sub-acute thrombus, acute thrombus, or chronic thrombus, and
wherein the processor circuit is configured to output the intraluminal ultrasound image such that at least one of the sub-acute thrombus, acute thrombus, or chronic thrombus in the intraluminal ultrasound image is enhanced.

8. The system of claim 4, wherein the processor circuit is configured to identify the anatomical feature based on an occlusion threshold.

9. An intraluminal ultrasound imaging method, the method comprising:
with a processor circuit in communication with an intraluminal imaging catheter, a display, and a user interface:
receiving, via the user interface, a selection of a thrombus option or a stent option from a plurality of image type options, wherein the plurality of image type options comprises:
the thrombus option, wherein the thrombus option is associated with a gain curve comprising a first preset non-linear shape specific to the thrombus option; and
the stent option, wherein the the stent option is associated with the gain curve comprising a second preset non-linear shape specific to the stent option;
identifying the gain curve based on the selection such that the gain curve comprises;
the first preset non-linear shape specific to the thrombus option when the selection is of the thrombus option; or
the second preset non-linear shape specific to the stent option when the selection is of the stent option,
wherein the gain curve determines a visual aspect of how an intraluminal ultrasound image is displayed on the display;
outputting, to the display, a visual representation of the gain curve with the first preset non-linear shape or the second preset non-linear shape,
wherein the visual representation of the gain curve comprises:
a first axis comprising a plurality of values of an input intensity of a pixel;
a second axis comprising a plurality of values of an output intensity of the pixel; and
a plurality of data points along the first preset non-linear shape or the second preset non-linear shape,
wherein the plurality of data points is configured to be movable by a user to change:
a curvature of the gain curve from the first preset non-linear shape or the second preset non-linear shape to a user-defined shape; and
the visual aspect of how the intraluminal ultrasound image is displayed on the display;
receiving the intraluminal ultrasound image obtained by the intraluminal ultrasound imaging catheter while the intraluminal ultrasound imaging catheter is positioned within a patient; and
outputting, to the display, the intraluminal ultrasound image such that the intraluminal ultrasound image is displayed according to the visual aspect.

10. The method of claim 9,
wherein, when the selection is of the stent option, a stent in the intraluminal ultrasound image is enhanced, and
wherein, when the selection is of the thrombus option, a thrombus in the intraluminal ultrasound image is enhanced,
wherein the thrombus comprises at least one of sub-acute thrombus, acute thrombus, or chronic thrombus.

11. The method of claim 9,
wherein the selection is further changes at least one of ringdown, brightness, contrast, saturation, hue, field of view, or chroma.

12. The method of claim 10, further comprising:
outputting, to the display, a detection option associated with an anatomical feature, wherein the anatomical features comprises at least one of a thrombus or a webbing; and
identifying, the anatomical feature in the intraluminal ultrasound image in response to receiving a selection of the detection option.

13. The method of claim 12, wherein identifying the anatomical feature is based on an occlusion threshold.

14. An intravascular imaging system, comprising:
an intravascular imaging catheter configured to obtain an intravascular image; and
a processor circuit configured for communication with the intravascular imaging catheter, a display, and a user interface, wherein the processor circuit is configured to:
receive, via the user interface, a selection of a thrombus option or a stent option from a plurality of image type options, wherein the plurality of image type options comprises:

the thrombus option, wherein the thrombus option is associated with a gain curve comprising a first preset non-linear shape specific to the thrombus option; and the stent option, wherein the stent option is associated with the gain curve comprising a second preset non-linear shape specific to the stent option;

identify the gain curve based on the selection such that the gain curve comprises:

the first preset non-linear shape specific to the thrombus option when the selection is of the thrombus option; or the second preset non-linear shape specific to the stent option when the selection is of the stent option, wherein the gain curve determines a visual aspect of how the intravascular image is displayed on the display; and output, to the display, a visual representation of the gain curve with the first preset non-linear shape or the second preset non-linear shape, wherein the visual representation of the gain curve comprises:

a first axis comprising a plurality of values of an input intensity of a pixel;

a second axis comprising a plurality of values of an output intensity of the pixel; and a plurality of data points along the first preset non-linear shape or the second preset non-linear shape, wherein the plurality of data points is configured to be movable by a user to change:

a curvature of the gain curve from the first preset non-linear shape or the second preset non-linear shape to a user-defined shape; and the visual aspect of how the intravascular image is displayed on the display, wherein the processor circuit is configured to receive the intravascular image obtained by the intravascular imaging catheter while the intravascular imaging catheter is positioned within a blood vessel of a patient, wherein the processor circuit is configured to output, to the display, the intravascular image such that the intravascular image is displayed according to the visual aspect.

15. The system of claim 14,
wherein the thrombus option comprises a first thrombus option, and
wherein the plurality of image type options further comprises a different, second thrombus option.

16. The system of claim 14, wherein the plurality of image type options further comprises a deep vein thrombosis option.

17. The system of claim 14,
wherein the processor circuit is configured to output, to the display, a plurality of procedure type options,
wherein the plurality of procedure type options comprises a coronary vasculature option and a peripheral vasculature option.

18. The system of claim 15,
wherein the first thrombus option comprises an acute or sub-acute thrombus option, and
wherein the second thrombus option comprises a chronic thrombus option.

19. The system of claim 17,
wherein the peripheral vasculature option comprises a peripheral venous vasculature option, and
wherein the plurality of image type options comprises a set of image type options specific to peripheral venous vasculature.

20. The system of claim 17,
wherein the peripheral vasculature option comprises a peripheral venous option, and
wherein the plurality of procedure type options further comprises a peripheral arterial option.

21. The system of claim 17,
wherein the plurality of image type options comprises a first set of image type options specific to peripheral vasculature or a second set of image type options specific to coronary vasculature,
wherein the first set of image type options is different than the second set of image type options.

* * * * *